United States Patent
Saha et al.

(10) Patent No.: US 11,744,503 B2
(45) Date of Patent: Sep. 5, 2023

(54) LONG-DURATION ARRHYTHMIA DETECTION

(71) Applicant: Cardiac Pacemakers, Inc., St. Paul, MN (US)

(72) Inventors: Sunipa Saha, Shoreview, MN (US); David L. Perschbacher, Coon Rapids, MN (US); Deepa Mahajan, North Oaks, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 459 days.

(21) Appl. No.: 16/845,578

(22) Filed: Apr. 10, 2020

(65) Prior Publication Data

US 2020/0323459 A1    Oct. 15, 2020

Related U.S. Application Data (60) Provisional application No. 62/833,282, filed on Apr. 12, 2019.

(51) Int. Cl.
| | |
|---|---|
| *A61B 5/364* | (2021.01) |
| *A61B 5/00* | (2006.01) |
| *A61B 5/361* | (2021.01) |
| *A61B 5/349* | (2021.01) |
| *A61N 1/372* | (2006.01) |
| *A61N 1/365* | (2006.01) |
| *A61N 1/39* | (2006.01) |

(52) U.S. Cl.
CPC .............. *A61B 5/364* (2021.01); *A61B 5/349* (2021.01); *A61B 5/361* (2021.01); *A61B 5/686* (2013.01); *A61N 1/36592* (2013.01); *A61N 1/37211* (2013.01); *A61N 1/39* (2013.01)

(58) Field of Classification Search
None
See application file for complete search history.

(56) References Cited

U.S. PATENT DOCUMENTS

| | | | |
|---|---|---|---|
| 8,560,058 B2 | 10/2013 | Babaeizadeh et al. | |
| 9,999,368 B2 | 6/2018 | Perschbacher et al. | |
| 2006/0195037 A1 | 8/2006 | Wiesel | |
| 2010/0114203 A1* | 5/2010 | Burnes | A61N 1/39622 607/4 |
| 2011/0125206 A1 | 5/2011 | Bornzin et al. | |
| 2014/0330134 A1 | 11/2014 | Chon et al. | |
| 2015/0342466 A1* | 12/2015 | Thakur | A61B 5/361 600/528 |

(Continued)

OTHER PUBLICATIONS

"U.S. Appl. No. 16/845,552, Examiner Interview Summary dated Feb. 15, 2022", 2 pgs.

(Continued)

*Primary Examiner* — Kennedy Schaetzle
(74) *Attorney, Agent, or Firm* — Schwegman Lundberg & Woessner, P.A.

(57) ABSTRACT

This document discusses, among other things, systems and methods to detect an initial arrhythmia event indication and, after a threshold amount of detection window intervals detecting the initial arrhythmia event indication, adjust a set of arrhythmia parameters or at least one of a respective set of parameter thresholds to increase sensitivity of an extended arrhythmia event indication detection.

20 Claims, 5 Drawing Sheets

(56) References Cited

U.S. PATENT DOCUMENTS

2016/0045125 A1    2/2016   Krueger et al.
2017/0127965 A1    5/2017   Krueger et al.
2017/0290550 A1   10/2017   Perschbacher et al.
2017/0296076 A1   10/2017   Mahajan et al.
2018/0028086 A1*   2/2018   Cao ..................... A61N 1/3624
2018/0192902 A1    7/2018   Perschbacher et al.
2020/0323452 A1   10/2020   Mahajan et al.

OTHER PUBLICATIONS

"U.S. Appl. No. 16/845,552, Final Office Action dated May 2, 2022", 12 pgs.
"U.S. Appl. No. 16/845,552, Non Final Office Action dated Dec. 10, 2021", 10 pgs.
"U.S. Appl. No. 16/845,552, Response filed Mar. 9, 2022 to Non Final Office Action dated Dec. 10, 2021", 10 pgs.
"U.S. Appl. No. 16/845,552, Response filed Jul. 5, 2022 to Final Office Action dated May 2, 2022", 12 pgs.

* cited by examiner

LONG-DURATION ARRHYTHMIA DETECTION

CLAIM OF PRIORITY

This application claims the benefit of priority under 35 U.S.C. § 119(e) of U.S. Provisional Patent Application Ser. No. 62/833,282, filed on Apr. 12, 2019, which is herein incorporated by reference in its entirety.

TECHNICAL FIELD

This document relates generally to medical devices, and more particularly, but not by way of limitation, to systems, devices, and methods for long-duration arrhythmia detection.

BACKGROUND

Heart failure (HF) is a reduction in the ability of the heart to deliver enough blood to meet bodily needs. HF patients commonly have enlarged heart with weakened cardiac muscles, resulting in reduced contractility and poor cardiac output of blood. Signs of HF include pulmonary congestion, edema, difficulty breathing, etc. HF is often a chronic condition, but can also occur suddenly, affecting the left, right, or both sides of a heart. Causes of HF include, among others, coronary artery disease, myocardial infarction, high blood pressure, atrial fibrillation, valvular heart disease, alcoholism, infection, cardiomyopathy, or one or more other conditions leading to a decreased pumping efficiency of the heart.

An arrhythmia is an abnormal heart rhythm, or any heart rhythm (e.g., fast, slow, irregular, etc.) that is not a normal heart rhythm. Arrhythmias include, among others: bradycardia; tachycardia; premature, extra, or skipped heart beats; heart defects; and atrial or ventricular fibrillation affecting one or more chambers of the heart. Atrial fibrillation (AF) is as an abnormal heart rhythm characterized by rapid and irregular activity in the left or right atria of the heart. AF is commonly associated with a reduction in cardiac output, an increased risk of heart failure (HF), dementia, and stroke. Risk factors for AF include, among others, high blood pressure, heart failure (HF), valvular heart disease, COPD, obesity, and sleep apnea.

An ambulatory medical device (AMD), such as an implantable, wearable, or other external medical device, can be configured to monitor, detect, or treat various conditions, including HF, arrhythmias, etc.

SUMMARY

This document discusses, among other things, systems and methods to detect an initial arrhythmia event indication and, after a threshold amount of detection window intervals detecting the initial arrhythmia event indication, adjust a set of arrhythmia parameters or at least one of a respective set of parameter thresholds to increase sensitivity of an extended arrhythmia event indication detection.

Example 1 is a system, comprising: a signal receiver circuit configured to receive cardiac electrical information of a subject; and an assessment circuit configured to perform event detection, comprising to: determine a set of arrhythmia parameters for a detection window interval using the received cardiac electrical information of the subject, the set including at least one arrhythmia parameter; and detect, for the detection window interval, an initial arrhythmia event indication using the determined set of arrhythmia parameters and a respective set of parameter thresholds, wherein, after a threshold amount of detection window intervals detecting the initial arrhythmia event indication, the assessment circuit is configured to adjust the event detection, comprising to: adjust the set of arrhythmia parameters or at least one of the respective set of parameter thresholds to increase sensitivity of an extended arrhythmia event indication detection using the adjusted set of arrhythmia parameters or at least one of the respective set of parameter thresholds.

In Example 2, the subject matter of Example 1 optionally includes wherein the threshold amount of detection window intervals detecting the initial arrhythmia event indication comprises a threshold amount of successive detection window intervals detecting the initial arrhythmia event indication.

In Example 3, the subject matter of Example 2 optionally includes wherein the assessment circuit is configured to detect, for a subsequent detection window interval, subsequent to the successive detection window intervals, an extended arrhythmia event indication using the adjusted set of arrhythmia parameters.

In Example 4, the subject matter of any one or more of Examples 2-3 optionally include wherein the assessment circuit is configured to detect, for a subsequent detection window interval, subsequent to the successive detection window intervals, an extended arrhythmia event indication using the adjusted at least one of the respective set of parameter thresholds.

In Example 5, the subject matter of any one or more of Examples 2-4 optionally include wherein the assessment circuit is configured to adjust the set of arrhythmia parameters and at least one of the respective set of parameter thresholds to increase sensitivity of an extended arrhythmia event indication detection.

In Example 6, the subject matter of Example 5 optionally includes wherein the assessment circuit is configured to detect, for a subsequent detection window interval, subsequent to the successive detection window intervals, an extended arrhythmia event indication using the adjusted set of arrhythmia parameters and the adjusted at least one of the respective set of parameter thresholds.

In Example 7, the subject matter of any one or more of Examples 2-6 optionally include wherein, to determine the set of arrhythmia parameters, the assessment circuit is configured to determine a first set of arrhythmia parameters, wherein, to detect the initial arrhythmia event indication, the assessment circuit is configured to detect the initial arrhythmia event indication using the determined first set of arrhythmia parameters and respective parameter thresholds, wherein, to adjust the event detection, the assessment circuit is configured to: determine a second set of arrhythmia parameters for a subsequent detection window interval, subsequent to the successive detection window intervals using the received cardiac electrical information of the subject, the second set smaller than the first set and including at least one arrhythmia parameter; and detect, for the subsequent detection window interval, an extended arrhythmia event indication using the determined second set of arrhythmia parameters using the determined second set of arrhythmia parameters and respective parameter thresholds.

In Example 8, the subject matter of any one or more of Examples 2-7 optionally include wherein, to adjust the event detection, the assessment circuit is configured to: adjust at least one of the respective set of parameter thresholds; and detect, for a subsequent detection window interval, subsequent to the successive detection window intervals, an extended arrhythmia event indication using the determined set of arrhythmia parameters and the adjusted at least one of the respective set of parameter thresholds.

In Example 9, the subject matter of any one or more of Examples 1-8 optionally include wherein the threshold amount of detection window intervals detecting the initial arrhythmia event indication comprises the threshold amount in a first number of detection windows.

In Example 10, the subject matter of any one or more of Examples 1-9 optionally include wherein the event detection includes atrial fibrillation (AF) detection, wherein the adjusted event detection includes a long-duration AF event detection, and wherein the threshold amount is at least one of a time threshold or a counter threshold.

Example 11 is a method, comprising: receiving, using a signal receiver circuit, cardiac electrical information of a subject; and performing, using an assessment circuit configured, event detection, comprising: determining a set of arrhythmia parameters for a detection window interval using the received cardiac electrical information of the subject, the set including at least one arrhythmia parameter; and detecting, for the detection window interval, an initial arrhythmia event indication using the determined set of arrhythmia parameters and a respective set of parameter thresholds, adjusting the event detection, using the assessment circuit, after a threshold amount of detection window intervals detecting the initial arrhythmia event indication, the adjusting the event detection comprising: adjusting the set of arrhythmia parameters or at least one of the respective set of parameter thresholds to increase sensitivity of an extended arrhythmia event indication detection using the adjusted set of arrhythmia parameters or at least one of the respective set of parameter thresholds.

In Example 12, the subject matter of Example 11 optionally includes wherein adjusting, after the threshold the threshold amount of detection window intervals detecting the initial arrhythmia event indication comprises adjusting after a threshold amount of successive detection window intervals detecting the initial arrhythmia event indication.

In Example 13, the subject matter of Example 12 optionally includes detecting, for a subsequent detection window interval, subsequent to the successive detection window intervals, an extended arrhythmia event indication using the adjusted set of arrhythmia parameters.

In Example 14, the subject matter of any one or more of Examples 12-13 optionally include detecting, for a subsequent detection window interval, subsequent to the successive detection window intervals, an extended arrhythmia event indication using the adjusted at least one of the respective set of parameter thresholds.

In Example 15, the subject matter of any one or more of Examples 12-14 optionally include wherein adjusting the event detection comprises: adjusting the set of arrhythmia parameters and at least one of the respective set of parameter thresholds to increase sensitivity of an extended arrhythmia event indication detection.

In Example 16, the subject matter of Example 15 optionally includes detecting, for a subsequent detection window interval, subsequent to the successive detection window intervals, an extended arrhythmia event indication using the adjusted set of arrhythmia parameters and the adjusted at least one of the respective set of parameter thresholds.

In Example 17, the subject matter of any one or more of Examples 12-16 optionally include wherein determining the set of arrhythmia parameters comprises determining a first set of arrhythmia parameters, wherein detecting the initial arrhythmia event indication comprises detecting the initial arrhythmia event indication using the determined first set of arrhythmia parameters and respective parameter thresholds, wherein adjusting the event detection comprises: determining a second set of arrhythmia parameters for a subsequent detection window interval, subsequent to the successive detection window intervals using the received cardiac electrical information of the subject, the second set smaller than the first set and including at least one arrhythmia parameter; and detecting, for the subsequent detection window interval, an extended arrhythmia event indication using the determined second set of arrhythmia parameters using the determined second set of arrhythmia parameters and respective parameter thresholds.

In Example 18, the subject matter of any one or more of Examples 12-17 optionally include wherein adjusting the event detection comprises: adjusting at least one of the respective set of parameter thresholds; and detecting, for a subsequent detection window interval, subsequent to the successive detection window intervals, an extended arrhythmia event indication using the determined set of arrhythmia parameters and the adjusted at least one of the respective set of parameter thresholds.

Example 19 is a system, comprising: a signal receiver circuit configured to receive cardiac electrical information of a subject; and an assessment circuit configured to perform event detection, comprising: determine a first set of arrhythmia parameters for a detection window interval using the received cardiac electrical information of the subject; and detect, for the detection window interval, an initial arrhythmia event indication using the determined first set of arrhythmia parameters and respective parameter thresholds; wherein, after a threshold amount of successive detection window intervals detecting the initial arrhythmia event indication, the assessment circuit is configured to adjust the event detection, comprising: determine a second set of arrhythmia parameters for a subsequent detection window interval, subsequent to the successive detection window intervals using the received cardiac electrical information of the subject, the second set smaller than the first set and including at least one arrhythmia parameter; and detect, for the subsequent detection window interval, an extended arrhythmia event indication using the determined second set of arrhythmia parameters using the determined second set of arrhythmia parameters and respective parameter thresholds.

Example 20 is a system, comprising: a signal receiver circuit configured to receive cardiac electrical information of a subject; and an assessment circuit configured to perform event detection, comprising: determine a set of arrhythmia parameters for a detection window interval using the received cardiac electrical information of the subject, the set including at least one arrhythmia parameter; and detect, for the detection window interval, an initial arrhythmia event indication using the determined set of arrhythmia parameters and a respective set of parameter thresholds; wherein, after a threshold amount of successive detection window intervals detecting the initial arrhythmia event indication, the assessment circuit is configured to adjust the event detection, comprising: adjust at least one of the respective set of parameter thresholds; and detect, for a subsequent detection window interval, subsequent to the successive detection window intervals, an extended arrhythmia event indication using the determined set of arrhythmia parameters and the adjusted at least one of the respective set of parameter thresholds.

In Example 21, subject matter (e.g., a system or apparatus) may optionally combine any portion or combination of any portion of any one or more of Examples 1-20 to comprise "means for" performing any portion of any one or more of the functions or methods of Examples 1-20, or at least one "non-transitory machine-readable medium" including instructions that, when performed by a machine, cause the machine to perform any portion of any one or more of the functions or methods of Examples 1-20.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Arrhythmia events, including potential arrhythmia events, such as atrial fibrillation (AF) events or potential events, can be detected using cardiac electrical information, including, for example, detected atrial or ventricular events (e.g., beats, r-waves, p-waves, etc.) or intervals therebetween occurring within a detection window, often between 30 seconds and 2 minutes, though in certain examples longer or shorter. Ambulatory, implantable, subcutaneous, wearable, or other medical devices can determine that AF is present or not for each detection window.

Long-duration arrhythmias, including long-duration atrial arrhythmias including AFs, atrial tachyarrhythmias (ATs), or one or more other long-duration events, are periods of continuously detected events (e.g., detection in successive detection windows, or detection in A of B detection windows, such as detection in 7 of 10 detection windows, 8 of 10 detection windows, 9 of 10 detection windows, etc.) and are often associated with a statistically significant increased risk of stroke and systemic embolization. The interval of a long-duration event (a long-duration interval) can refer, in certain examples, to a duration of or longer than 18 hours. In other examples, the long-duration interval can refer to longer or shorter durations, such as a duration of or longer than 24 hours, 12 hours, 6 hours, 4 hours, 2 hours, 1 hour, etc. Different duration intervals can be associated with different indications, detection, monitoring, or treatment parameters, etc. There are often many individual detection windows (e.g., 30 seconds, 2 minutes, etc.) in a single long-duration interval. For example, there are 540 2-minute detection windows in an 18-hour long-duration interval. However, a single missed detection in one of the many individual detection windows of a long-duration interval may result in a determination of no long-duration event, or multiple events of varying duration (e.g., varying lengths of successive (or detection in A of B) detection windows, etc.), in certain examples affecting device performance, resource allocation (e.g., storage, processing, sensors, etc.), device longevity, etc. In an example, instead of successive detection windows, a threshold number of detections (A) in a detection period (B) (or window) can be used.

Figure 1:
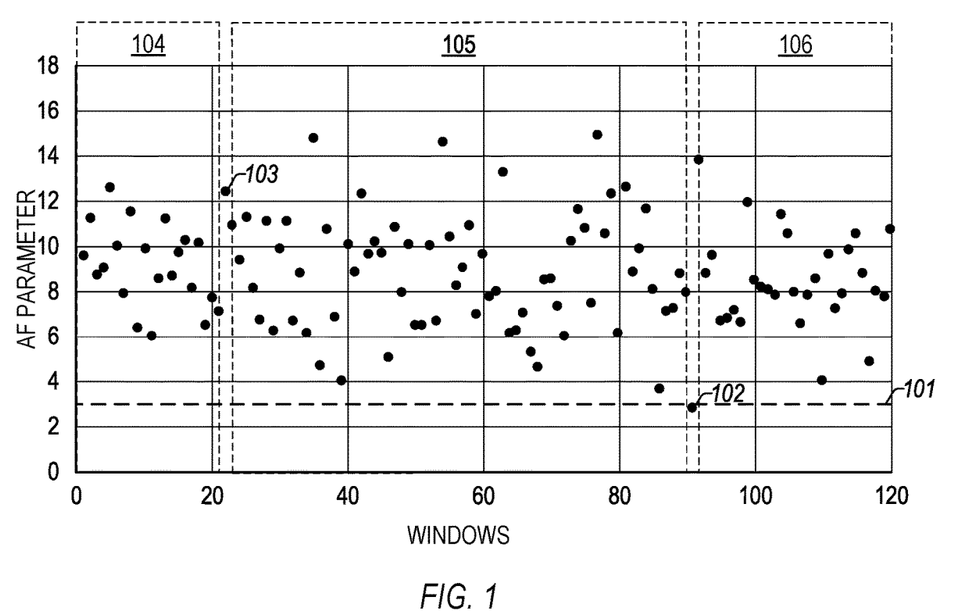
FIG. 1 illustrates an example missed long-duration event.

FIG. 1 illustrates an example relationship 100 of measures of an arrhythmia parameter for specific detection windows. Each data point (black circles) represents an indication of a received or determined arrhythmia parameter for a respective detection window. The arrhythmia parameters can include measures of diastolic dysfunction (DD) or one or more other arrhythmia parameters. FIG. 1 illustrates 120 detection windows, which, given 2-minute detection windows, represents 4 hours of event detection. In an example, 4 hours can represent a long-duration interval. In other examples, other length long-duration intervals or detection windows can be used.

The relationship 100 illustrates a lower detection threshold 101. Indications of arrhythmia parameters below the lower detection threshold 101 are not indicative of an arrhythmia (e.g., AF) event (or potential event), or are not indicative of an arrhythmia event degree of clinical relevance (e.g., <50%, <70%, <90%, etc.). In other examples, arrhythmia parameters above the lower detection threshold 101 are indicative of an arrhythmia event (or potential event) within a degree of certainty (e.g., >50%, >70%, >90%, etc., for example, based on population data or for a respective subject, etc.).

A first data point 102 is below the lower detection threshold 101, and accordingly, can be rejected. In other examples, multiple data points at or near the value of the first data point 102 can follow, such that a series of data points are below the lower detection threshold 101. In other examples, data points can be rejected for one or more other reasons, separate from the lower detection threshold 101, such as signal quality issues (e.g., noise, motion artifacts, etc.), rate or interval thresholds, etc. For example, in FIG. 1, a second data point 103 is rejected for failing signal quality issues (e.g., background noise, motion artifacts, etc.). The first and second data points 102, 103 separates what would otherwise be a long-duration event at or greater than a long-duration interval (e.g., 4 hours, etc.) into two or three separate, shorter-duration (in contrast) events (e.g., first, second, and third multiple-detection-window events 104, 105, 106). Upon certain conditions, the long-duration event can be missed in its entirety.

In an example, hysteresis can be implemented in the event detection, such that a number of rejected data points can be tolerated before leaving an event state. While such hysteresis may account for a small number of noisy detection windows, such counts fail to adequately address borderline cases, successive periods of noise, motion, activity, etc., affecting a number of values at or near a detection threshold greater than the hysteresis.

The present inventors have recognized, among other things, that one or more arrhythmia detection parameters can be dynamically changed based on the duration of a detected event, or presentation of one or more other arrhythmia-related parameters, such as atrial flutter, etc., to improve detection of long-duration arrhythmia events, including long-duration atrial arrhythmias, long-duration AF, etc. As a duration of the long-duration event extends (e.g., while in a detected event (or potential event) state), the likelihood of a continued event increases, and therefore detection parameters can be modified, changed, or otherwise adjusted to continue detection of the long-duration event. As the likelihood of the continued event increases, the sensitivity of event detection can decrease (e.g., commensurate with the increased likelihood of the continued event), without negatively affecting the sensitivity of event detection in a particular detection window, and increasing the sensitivity of long-duration event detection for the long-duration interval. The sensitivity of event detection in a single detection window is different than the sensitivity of long-duration event detection in a long-duration interval. Detections in each specific detection window have a specific confidence (e.g., due to detection variations, signal quality issues, etc.). The confidence of successive detection windows can be lower than each specific window.

For example, long-duration events can be detected using X of Y criteria or detection parameters, or with a combination of different arrhythmia detection parameters or algorithms (e.g., AF, AT, or atrial flutter detection parameters or algorithms, etc.). For example, AF detection can be more a more-specific long-duration event detection, and AT detection can be a more-sensitive long-duration event detection, such as in contrast to each other. Combinations of arrhythmia detections (e.g., detection algorithms, etc.) can be used to detect events, with one or more detection parameters or criteria modified, changed, or adjusted in time to maintain long-duration event detection, or to reduce the likelihood of a missed long-duration event. In other examples, multiple detections can be used to detect an event with initial low sensitivity or high specificity, and, as the duration of the event increases, less detections can be used, or detection parameters can be adjusted, to increase sensitivity or decrease specificity, such as to maintain uninterrupted detection of a long-duration event, increasing the likelihood of detecting a long-duration event.

In other examples, as the duration of a detected event increases, additional criteria can be required to exit an event. For example, if multiple detections are used, then more than one detection can be required for a rejected data point. In an example, a single detection criteria or event detection can be required to detect an event, and multiple detection criteria can be required to reject the event. In certain examples, rejection criteria can become more stringent as time passes, such that it becomes more difficult (e.g., increasing with time, in one or more steps, etc.) to leave an event than it is to enter an event. For example, a first number of criteria can be required to enter an event state (e.g., detected indication of an AF event or possible AF event) and a second number, higher than the first number, can be required to leave the event state (e.g., detected indication of a non-AF event or possible non-AF event).

Arrhythmia detection can include an initial trigger or detection of a potential arrhythmia event (e.g., an AF event) and subsequent classification or confirmation of the initial triggered or detected potential arrhythmia event as an arrhythmia event. For shorter intervals, having an interval shorter than the long-duration interval, specificity can be maintained, avoiding false positives. As the duration lengthens, one or more detection criteria or thresholds can be changed (e.g., dynamically), such as within pre-defined guidelines or boundaries. In an example, detection criteria and thresholds may not be lowered past a highest sensitivity (e.g., a most sensitive setting). In other examples, specificity may not be lowered past a lowest specificity (e.g., a least specific setting). Criteria and thresholds can be readjusted when an indication of an arrhythmia parameter not indicative of an arrhythmia event (e.g., a low-confidence AF detection window, etc.) is received or determined.

In certain examples, dynamic changes of detection criteria or parameters can improve long-duration event detection in ambulatory medical devices, reducing service burden of the device, as multiple, separate events are not unnecessarily stored or reported for a single or smaller number of events. In other examples, as the duration of a single event (e.g., a long-duration event) increases, specificity of detection can decrease, reducing required processing resources, lowering power consumption, and extending the life of the ambulatory medical device. In an example, after a threshold time period (e.g., after 10 minutes of consecutive periods of detected AF) or a number of positive event windows, morphology evaluation of the received cardiac electrical information (e.g., comparison of the received cardiac electrical information to a template, etc.) may cease, reducing required resources to maintain event detection, reducing the likelihood that an event window or data point is rejected due to noise, determination of one or more premature ventricular contractions (PVCs), etc. Further, storage requirements may be smaller for a single, long-duration event than for multiple shorter-duration events. In certain examples, only the head and the tail of each event (long or short) are stored for later review by an external medical device or a clinician. Accurately detecting long-duration events as a single, long-duration event instead of separate, shorter-duration events can improve the storage capabilities of the system. Moreover, improved detection of conditions or detection of additional conditions in sophisticated, regulatory-compliant medical systems, components, or machinery may increase the efficiency of medical system resources, improving the functioning of modern regulated technological systems and methods not capable of being performed or managed by generic computers, components, or machinery.

Examples of AF detection algorithms, including various AF detection parameters and criteria, can be found, for example, in the commonly assigned Krueger et al. U.S. patent application Ser. No. 14/825,669, titled "Atrial Fibrillation Detection Using Ventricular Rate Variability" (herein, "the '669 application"); Perschbacher et al. U.S. patent application Ser. No. 15/082,440, titled "Atrial Fibrillation Detection" (herein, "the '440 application"); Krueger et al. U.S. patent application Ser. No. 15/341,565, titled "Method and Apparatus for Enhancing Ventricular Based Atrial Fibrillation Detection Using Atrial Activity" (herein, "the '565 application"); and Perschbacher et al. U.S. patent application Ser. No. 15/864,953, titled "Atrial Fibrillation Discrimination Using Heart Rate Clustering" (herein, "the '953 application"), each of which are hereby incorporated by reference in their entireties, including their disclosure of AF detection and AF detection algorithms including, for example: AF detection using pairs of ventricular information detected from a ventricle, including rate changes and rate change characteristics, and determination of valid heart beats or intervals using various characteristics, including threshold rates, intervals, morphology criterion, etc., such as disclosed in the '669 application; AF detection using a distribution of ventricular depolarization intervals, such as disclosed in the '440 application; AF detection using atrial activity scores from an atrial detection window prior to a detected ventricular polarization, such as disclosed in the '565 application; AF discrimination using clustered depolarization information, such as disclosed in the '953 application, etc.

Ambulatory medical devices (AMDs), including implantable or wearable medical devices, can be configured to monitor, detect, or treat various cardiac conditions associated with a reduced ability of a heart to sufficiently deliver blood to a body, such HF, arrhythmias, hypertension, etc. An AMD can include a single device or a plurality of medical devices or monitors implanted in a subject's body or otherwise positioned on or about the subject to monitor subject physiologic information of the subject, such as heart sounds, respiration (e.g., respiration rate, tidal volume, etc.), impedance (e.g., thoracic impedance, cardiac impedance, etc.), pressure (e.g., blood pressure), cardiac activity (e.g., heart rate), physical activity, posture, plethysmography, or one or more other physiologic parameters of a subject, or to provide electrical stimulation or one or more other therapies or treatments to optimize or control contractions of the heart.

In an example, the AMD can include one or more of: a respiration sensor configured to receive respiration information (e.g., a respiration rate (RR), a respiration volume (tidal volume), etc.); an acceleration sensor (e.g., an accelerometer, a microphone, etc.) configured to receive cardiac acceleration information (e.g., cardiac vibration information, pressure waveform information, heart sound information, endocardial acceleration information, acceleration information, activity information, posture information, etc.); an impedance sensor (e.g., intrathoracic impedance sensor, transthoracic impedance sensor, etc.) configured to receive impedance information, a cardiac sensor configured to receive cardiac electrical information; an activity sensor configured to receive information about a physical motion (e.g., activity, steps, etc.); a posture sensor configured to receive posture or position information; a pressure sensor configured to receive pressure information; a plethysmograph sensor (e.g., a photoplethysmography sensor, etc.); a chemical sensor; or one or more other sensors configured to receive physiologic information of the subject.

Traditional cardiac rhythm management (CRM) devices, such as pacemakers, defibrillators, or cardiac resynchronizers, include subcutaneous devices configured to be implanted in a chest of a subject, having one or more leads to position one or more electrodes or other sensors at various locations in or near the heart, such as in one or more of the atria or ventricles. Separate from, or in addition to, the one or more electrodes or other sensors of the leads, the CRM device can include one or more electrodes or other sensors (e.g., a pressure sensor, an accelerometer, a gyroscope, a microphone, etc.) powered by a power source in the CRM device. The one or more electrodes or other sensors of the leads, the CRM device, or a combination thereof, can be configured detect physiologic information from, or provide one or more therapies or stimulation to, the subject.

Implantable devices can additionally include leadless cardiac pacemakers (LCP), small (e.g., smaller than traditional implantable CRM devices, in certain examples having a volume of about 1 cc, etc.), self-contained devices including one or more sensors, circuits, or electrodes configured to monitor physiologic information (e.g., heart rate, etc.) from, detect physiologic conditions (e.g., tachycardia) associated with, or provide one or more therapies or stimulation to the heart without traditional lead or implantable CRM device complications (e.g., required incision and pocket, complications associated with lead placement, breakage, or migration, etc.). In certain examples, an LCP can have more limited power and processing capabilities than a traditional CRM device; however, multiple LCP devices can be implanted in or about the heart to detect physiologic information from, or provide one or more therapies or stimulation to, one or more chambers of the heart. The multiple LCP devices can communicate between themselves, or one or more other implanted or external devices.

Wearable or external medical sensors or devices can be configured to detect or monitor physiologic information of the subject without required implant or an in-patient procedure for placement, battery replacement, or repair. However, such sensors and devices, in contrast to implantable medical devices, may have reduced patient compliance, increased detection noise, or reduced detection sensitivity.

For each ambulatory medical device (AMD) described above (e.g., implantable medical device (IMD) or wearable medical devices (WMD)), each additional sensor can increase system cost and complexity, reduce system reliability, or increase the power consumption and reduce the usable life of the ambulatory device. Accordingly, it can be beneficial to use a single sensor to determine multiple types of physiologic information, or a smaller number of sensors to measure a larger number of different types of physiologic information.

Figure 2:
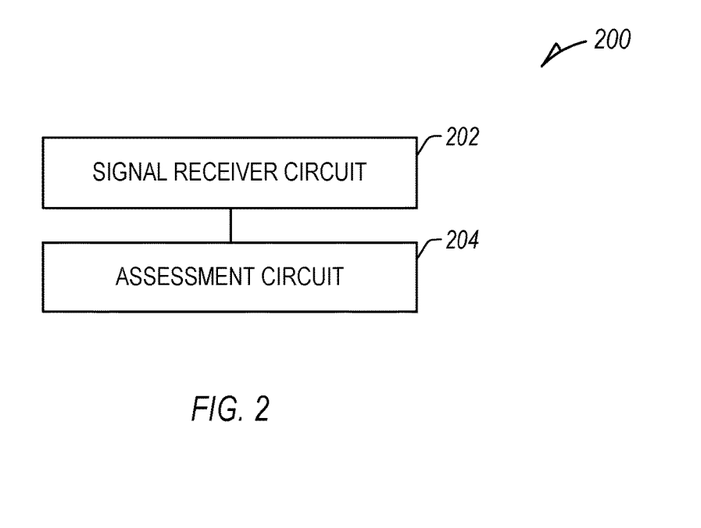
FIG. 2 illustrates an example medical-device system including a signal receiver circuit and an assessment circuit.

FIG. 2 illustrates an example system (e.g., a medical device, etc.) 200 including a signal receiver circuit 202 and an assessment circuit 204, each having an input and an output. The signal receiver circuit 202 can be configured to receive subject information, such as physiologic information of a subject, a patient (or a group of subjects or patients) from one or more sensors. In an example, the signal receiver circuit can be configured to receive cardiac electrical information of the subject, such as from a cardiac sensor (e.g., including one or more electrodes configured to sense electrical activity of the subject, such as cardiac electrical activity, and an amplifier configured to amplify the received cardiac electrical activity, etc.) or one or more other devices or sensors, etc.

The assessment circuit 204 can be configured to receive information from the signal receiver circuit 202, and to determine one or more parameters (e.g., composite physiologic parameters, stratifiers, one or more pacing parameters, etc.), such as described herein. In an example, the assessment circuit 204 can be configured to detect an arrhythmia event (or potential event) of the subject, such as an atrial fibrillation (AF) event or one or more other atrial arrhythmias, such as atrial tachyarrhythmia (AT), atrioventricular (AV) block (e.g., Wenckebach, etc.), atrial flutter (AFL), etc. using the received cardiac electrical information. In an example, the assessment circuit 204 can be configured to adjust the detection using a length, period of time, or a number of detection windows of the detected event (or potential event).

The assessment circuit 204 can be configured to determine a subject condition, or an indication, risk, or stratification of worsening subject condition, using the received information. The assessment circuit 204 can provide acute or chronic monitoring of the subject condition, and in certain examples can be configured to provide an output to a user, such as a score, an alert, a trend, or indication to the subject or a clinician. In certain examples, the assessment circuit 204 can be configured to provide an indication that the subject seek medical treatment or be hospitalized in response to a determined change, or otherwise determine one or more therapy parameters, such as to be provided to a clinician for consideration, or to propose, control, or otherwise manage one or more therapies to the subject or one or more functions, modes, or operations of one or more components of a medical-device system. In other examples, the assessment circuit 204 can be configured to provide an output to another circuit, machine, or process, such as to control, adjust, or cease a therapy of a medical device, a drug delivery system, etc., or otherwise alter one or more processes or functions of a medical-device system, such as to reduce use of system resources, etc.

Figure 3:
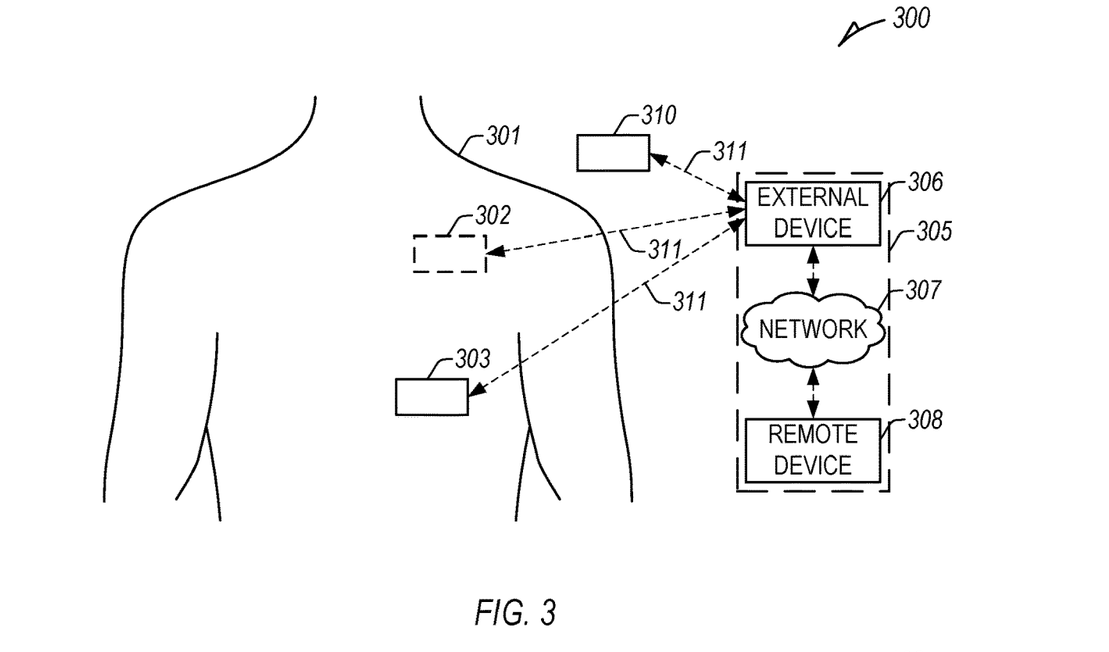
FIG. 3 illustrates an example patient management system and portions of an environment in which the system may operate.

FIG. 3 illustrates an example patient management system 300 and portions of an environment in which the system 300 may operate. The patient management system 300 can perform a range of activities, including remote patient monitoring and diagnosis of a disease condition. Such activities can be performed proximal to a patient 301, such as in a patient home or office, through a centralized server, such as in a hospital, clinic, or physician office, or through a remote workstation, such as a secure wireless mobile computing device.

The patient management system 300 can include one or more ambulatory devices, an external system 305, and a communication link 311 providing for communication between the one or more ambulatory devices and the external system 305. The one or more ambulatory devices can include an implantable medical device (IMD) 302, a wearable medical device 303, or one or more other implantable, leadless, subcutaneous, external, wearable, or ambulatory medical devices configured to monitor, sense, or detect information from, determine physiologic information about, or provide one or more therapies to treat various cardiac conditions of the patient 301, such as high blood pressure, an ability of a heart to sufficiently deliver blood to a body, including atrial fibrillation (AF), congestive heart failure (CHF), hypertension, or one or more other cardiac or non-cardiac conditions (e.g., dehydration, hemorrhage, renal dysfunction, etc.).

In an example, the IMD 302 can include one or more traditional cardiac rhythm management (CRM) devices, such as a pacemaker or defibrillator, implanted in a chest of a subject, having a lead system including one or more transvenous, subcutaneous, or non-invasive leads or catheters to position one or more electrodes or other sensors (e.g., a heart sound sensor) in, on, or about a heart or one or more other position in a thorax, abdomen, or neck of the subject 301. In another example, the IMD 302 can include a monitor implanted, for example, subcutaneously in the chest of subject 301.

The IMD 302 can include an assessment circuit configured to detect or determine specific physiologic information of the subject 301, or to determine one or more conditions or provide information or an alert to a user, such as the subject 301 (e.g., a patient), a clinician, or one or more other caregivers. The IMD 302 can alternatively or additionally be configured as a therapeutic device configured to treat one or more medical conditions of the subject 301. The therapy can be delivered to the subject 301 via the lead system and associated electrodes or using one or more other delivery mechanisms. The therapy can include anti-arrhythmic therapy to treat an arrhythmia or to treat or control one or more complications from arrhythmias, such as syncope, congestive heart failure (CHF), or stroke, among others. In other examples, the therapy can include delivery of one or more drugs to the subject 301 using the IMD 302 or one or more of the other ambulatory devices. Examples of the anti-arrhythmic therapy include pacing, cardioversion, defibrillation, neuromodulation, drug therapies, or biological therapies, among other types of therapies. In other examples, therapies can include cardiac resynchronization therapy (CRT) for rectifying dyssynchrony and improving cardiac function in CHF patients. In some examples, the IMD 302 can include a drug delivery system, such as a drug infusion pump to deliver drugs to the patient for managing arrhythmias or complications from arrhythmias, hypertension, or one or more other physiologic conditions. In yet other examples, the IMD 302 can include a therapy circuit or module configured to treat hypertension (e.g., a neurostimulation therapy circuit, a drug delivery therapy circuit, a stimulation therapy circuit, etc.).

The wearable medical device 303 can include one or more wearable or external medical sensors or devices (e.g., automatic external defibrillators (AEDs), Holter monitors, patch-based devices, smart watches, smart accessories, wrist- or finger-worn medical devices, such as a finger-based photoplethysmography sensor, etc.). In other examples, the wearable medical device 303 can include an acoustic sensor or accelerometer to detect acoustic information (e.g., heart sounds) or the sound or vibration of blood flow, an impedance sensor to detect impedance variations associated with changes in blood flow or volume, a temperature sensor to detect temperature variation associated with blood flow, a laser Doppler vibrometer or other pressure, strain, or physical sensor to detect physical variations associated with blood flow, etc.

The patient management system 300 can include, among other things, a respiration sensor configured to receive respiration information (e.g., a respiration rate (RR), a respiration volume (tidal volume), etc.), a heart sound sensor configured to receive heart sound information, a thoracic impedance sensor configured to receive impedance information, a cardiac sensor configured to receive cardiac electrical information, an activity sensor configured to receive information about a physical motion (e.g., activity, posture, etc.), a plethysmography sensor, or one or more other sensors configured to receive physiologic information of the subject 301.

The external system 305 can include a dedicated hardware/software system, such as a programmer, a remote server-based patient management system, or alternatively a system defined predominantly by software running on a standard personal computer. The external system 305 can manage the subject 301 through the IMD 302 or one or more other ambulatory devices connected to the external system 305 via a communication link 311. In other examples, the IMD 302 can be connected to the wearable device 303, or the wearable device 303 can be connected to the external system 305, via the communication link 311. This can include, for example, programming the IMD 302 to perform one or more of acquiring physiological data, performing at least one self-diagnostic test (e.g., a device operational status, etc.), analyzing the physiological data to detect a cardiac arrhythmia, or optionally delivering or adjusting a therapy to the subject 301. Additionally, the external system 305 can send information to, or receive information from, the IMD 302 or the wearable device 303 via the communication link 311. Examples of the information can include real-time or stored physiological data from the subject 301, diagnostic data, such as detection of cardiac arrhythmias or events of worsening heart failure, responses to therapies delivered to the subject 301, or device operational status of the IMD 302 or the wearable device 303 (e.g., battery status, lead impedance, etc.). The communication link 311 can be an inductive telemetry link, a capacitive telemetry link, or a radio-frequency (RF) telemetry link, or wireless telemetry based on, for example, "strong" Bluetooth or IEEE 802.11 wireless fidelity "Wi-Fi" interfacing standards. Other configurations and combinations of patient data source interfacing are possible.

By way of example and not limitation, the external system 305 can include an external device 306 in proximity of the one or more ambulatory devices, and a remote device 308 in a location relatively distant from the one or more ambulatory devices, in communication with the external device 306 via a communication network 307. Examples of the external device 306 can include a medical device programmer.

The remote device 308 can be configured to evaluate collected subject or patient information and provide alert notifications, among other possible functions. In an example, the remote device 308 can include a centralized server acting as a central hub for collected data storage and analysis. The server can be configured as a uni-, multi-, or distributed computing and processing system. The remote device 308 can receive data from multiple subjects or patients. The data can be collected by the one or more ambulatory devices, among other data acquisition sensors or devices associated with the subject 301. The server can include a memory device to store the data in a patient database. The server can include an alert analyzer circuit to evaluate the collected data to determine if specific alert condition is satisfied. Satisfaction of the alert condition may trigger a generation of alert notifications, such to be provided by one or more human-perceptible user interfaces. In some examples, the alert conditions may alternatively or additionally be evaluated by the one or more ambulatory devices, such as the IMD. By way of example, alert notifications can include a Web page update, phone or pager call, E-mail, SMS, text or "Instant" message, as well as a message to the subject or patient and a simultaneous direct notification to emergency services and to the clinician. Other alert notifications are possible. The server can include an alert prioritizer circuit configured to prioritize the alert notifications. For example, an alert of a detected medical event can be prioritized using a similarity metric between the physiological data associated with the detected medical event to physiological data associated with the historical alerts.

The remote device 308 may additionally include one or more locally configured clients or remote clients securely connected over the communication network 307 to the server. Examples of the clients can include personal desktops, notebook computers, mobile devices, or other computing devices. System users, such as clinicians or other qualified medical specialists, may use the clients to securely access stored patient data assembled in the database in the server, and to select and prioritize patients and alerts for health care provisioning. In addition to generating alert notifications, the remote device 308, including the server and the interconnected clients, may also execute a follow-up scheme by sending follow-up requests to the one or more ambulatory devices, or by sending a message or other communication to the subject 301 (e.g., the patient), clinician or authorized third party as a compliance notification.

The communication network 307 can provide wired or wireless interconnectivity. In an example, the communication network 307 can be based on the Transmission Control Protocol/Internet Protocol (TCP/IP) network communication specification, although other types or combinations of networking implementations are possible. Similarly, other network topologies and arrangements are possible.

One or more of the external device 306 or the remote device 308 can output the detected medical events to a system user, such as the patient or a clinician, or to a process including, for example, an instance of a computer program executable in a microprocessor. In an example, the process can include an automated generation of recommendations for anti-arrhythmic therapy, or a recommendation for further diagnostic test or treatment. In an example, the external device 306 or the remote device 308 can include a respective display unit for displaying the physiological or functional signals, or alerts, alarms, emergency calls, or other forms of warnings to signal the detection of arrhythmias. In some examples, the external system 305 can include an external data processor configured to analyze the physiological or functional signals received by the one or more ambulatory devices, and to confirm or reject the detection of arrhythmias. Computationally intensive algorithms, such as machine-learning algorithms, can be implemented in the external data processor to process the data retrospectively to detect cardia arrhythmias.

Portions of the one or more ambulatory devices or the external system 305 can be implemented using hardware, software, firmware, or combinations thereof. Portions of the one or more ambulatory devices or the external system 305 can be implemented using an application-specific circuit that can be constructed or configured to perform one or more functions or can be implemented using a general-purpose circuit that can be programmed or otherwise configured to perform one or more functions. Such a general-purpose circuit can include a microprocessor or a portion thereof, a microcontroller or a portion thereof, or a programmable logic circuit, a memory circuit, a network interface, and various components for interconnecting these components. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. "Sensors" can include electronic circuits configured to receive information and provide an electronic output representative of such received information.

The patient management system 300 can include a therapy device, such as a drug delivery device configured to provide therapy or therapy information (e.g., dosage information, etc.) to the subject 301, such as using information from one or more of the ambulatory devices. In other examples, one or more of the ambulatory devices can be configured to provide therapy or therapy information to the subject 301. The therapy device can be configured to send information to or receive information from one or more of the ambulatory devices or the external system 305 using the communication link 311. In an example, the one or more ambulatory devices, the external device 306, or the remote device 308 can be configured to control one or more parameters of the therapy device 310.

The external system 305 can allow for programming the one or more ambulatory devices and can receives information about one or more signals acquired by the one or more ambulatory devices, such as can be received via a communication link 311. The external system 305 can include a local external IMD programmer. The external system 305 can include a remote patient management system that can monitor patient status or adjust one or more therapies, such as from a remote location.

In various examples, the assessment circuit may be implemented using one or more of the IMD 302, the wearable medical device 303, or at the external system 305, such as using data extracted from the one or more ambulatory devices or data stored in a memory within the external system 305. In other examples, portions of the assessment circuit may be distributed between the one or more ambulatory devices and the external system 305.

Figure 4:
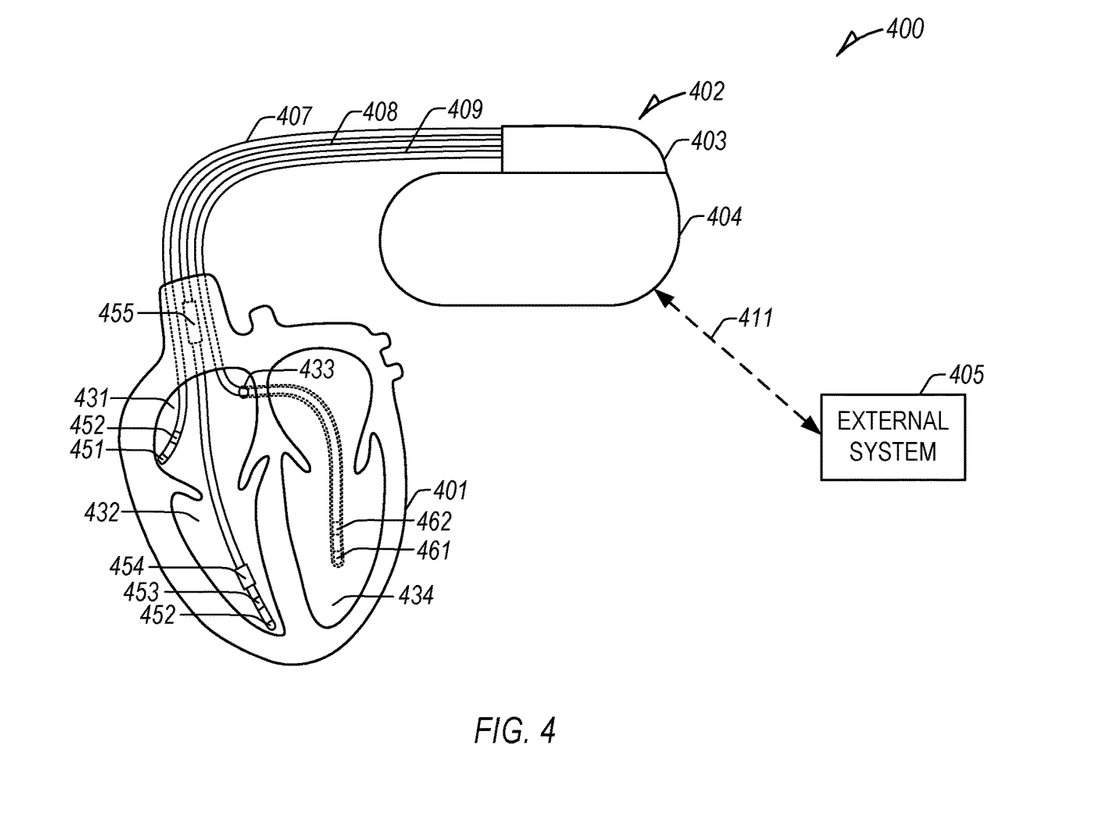
FIG. 4 illustrates an example of a Cardiac Rhythm Management (CRM) system and portions of an environment in which the CRM system can operate.

FIG. 4 illustrates an example of a Cardiac Rhythm Management (CRM) system 400 and portions of an environment in which the CRM system 400 can operate. The CRM system 400 can include an ambulatory medical device, such as an implantable medical device (IMD) 402 that can be electrically coupled to a heart 401 through one or more leads, such as one or more of a first, second, or third lead 407-409 coupled to the IMD 402 using a header 403, and an external system 405 that can communicate with the IMD 402, such as via a communication link 411.

The IMD 402 can include an implantable cardiac device, such as a pacemaker, an implantable cardioverter-defibrillator (ICD), or a cardiac resynchronization therapy defibrillator (CRT-D). The IMD 402 can include one or more monitoring or therapeutic devices, such as a subcutaneous implanted device, a wearable external device, a neural stimulator, a drug delivery device, a biological therapy device, or one or more other ambulatory medical devices. The IMD 402 may be coupled to or substituted by a monitoring medical device, such as a bedside or other external monitor.

The IMD 402 can include a hermetically sealed CAN 404 that can house an electronic circuit that can sense a physiologic signal in the heart 401 and can deliver one or more therapeutic electrical pulses to a target region, such as in the heart, through the one or more leads. In certain examples, the CRM system 400 can include only a single lead (e.g., the second lead 408, etc.), only two leads (e.g., the first and second leads 407, 408, or three or more leads, etc.

The first lead 407 can include a proximal end that can be configured to be connected to the IMD 402 and a distal end that can be configured to be placed at a target location, such as in the right atrium (RA) 431 of the heart 401. The first lead 407 can have a first pacing-sensing electrode 451 that can be located at or near its distal end, and a second pacing-sensing electrode 452 that can be located at or near the first pacing-sensing electrode 451. The first and second pacing-sensing electrodes 451, 452 can be electrically connected to the IMD 410, such as via separate conductors in the first lead 407, such as to allow for sensing of the right atrial activity and optional delivery of atrial pacing pulses.

The second lead 408 can be a defibrillation lead that can include a proximal end that can be connected to the IMD 410 and a distal end that can be placed at a target location, such as in the right ventricle (RV) 432 of the heart 401. The second lead 408 can have a first pacing-sensing electrode 452 that can be located at distal end, a second pacing-sensing electrode 453 that can be located near the first pacing-sensing electrode 452, a first defibrillation coil electrode 454 that can be located near the electrode 453, and a second defibrillation coil electrode 455 that can be located at a distance from the distal end, such as for superior vena cava (SVC) placement. The electrodes 452-455 can be electrically connected to the IMD 402, such as via separate conductors in the second lead 408. The first and second pacing-sensing electrodes 452, 453 can allow for sensing of a ventricular electrogram and can optionally allow delivery of one or more ventricular pacing pulses, and the first and second defibrillation coil electrodes 454, 455 can allow for delivery of one or more ventricular cardioversion/defibrillation pulses.

In an example, the second lead 408 can include only three electrodes. The first pacing-sensing electrode 452 and the first defibrillation coil electrode 454 can be used for sensing or delivery of one or more ventricular pacing pulses, and the electrodes the first defibrillation coil electrode 454 and the second defibrillation coil electrode 455 can be used for delivery of one or more ventricular cardioversion or defibrillation pulses.

The third lead 409 can include a proximal end that can be connected to the IMD 402 and a distal end that can be configured to be placed at a target location, such as in a left ventricle (LV) 434 of the heart 401. The third lead 409 may be implanted through the coronary sinus 433 and may be placed in a coronary vein over the LV, such as to allow for delivery of one or more pacing pulses to the LV. The third lead 409 can include a first distal electrode 461 that can be located at a distal end of the third lead 409 and a second distal electrode 462 that can be located near the first distal electrode 461. The first and second distal electrodes 461, 462 can be electrically connected to the IMD 402, such as via separate conductors in the third lead 409, such as to allow for sensing of the LV electrogram and optionally allow delivery of one or more resynchronization pacing pulses from the LV.

The IMD 402 can include an electronic circuit that can sense a physiologic signal. The physiologic signal can include an electrogram or a signal representing mechanical function of the heart 401. The hermetically sealed CAN 404 may function as an electrode, such as for sensing or pulse delivery. For example, an electrode from one or more of the first, second, or third leads 407-409 may be used together with the CAN 404, such as for unipolar sensing of an electrogram or for delivering one or more pacing pulses. A defibrillation electrode from the second lead 408 may be used together with the CAN 404, such as for delivering one or more cardioversion/defibrillation pulses.

In an example, the IMD 402 can sense impedance, such as between electrodes located on one or more of the first, second, or third leads 407-409 or the CAN 404. The IMD 402 can be configured to inject current between a pair of electrodes, sense the resultant voltage between the same or different pair of electrodes, and determine impedance using Ohm's Law. The impedance can be sensed in a bipolar configuration in which the same pair of electrodes can be used for injecting current and sensing voltage, a tripolar configuration in which the pair of electrodes for current injection and the pair of electrodes for voltage sensing can share a common electrode, or tetrapolar configuration in which the electrodes used for current injection can be distinct from the electrodes used for voltage sensing. In an example, the IMD 402 can be configured to inject current between an electrode on the second lead 408 and the CAN 404, and to sense the resultant voltage between the same electrodes or between a different electrode on the second lead 408 and the CAN 404. A physiologic signal can be sensed from one or more physiologic sensors that can be integrated within the IMD 402. The IMD 402 can also be configured to sense a physiologic signal from one or more external physiologic sensors or one or more external electrodes that can be coupled to the IMD 402. Examples of the physiologic signal can include one or more of heart rate, heart rate variability, intrathoracic impedance, intracardiac impedance, arterial pressure, pulmonary artery pressure, RV pressure, LV coronary pressure, coronary blood temperature, blood oxygen saturation, one or more heart sounds, physical activity or exertion level, physiologic response to activity, posture, respiration, body weight, or body temperature.

The arrangement and functions of these leads and electrodes are described above by way of example and not by way of limitation. Depending on the need of the subject and the capability of the implantable device, other arrangements and uses of these leads and electrodes are anticipated and included herein.

The external system 405 can allow for programming of the IMD 402 and can receives information about one or more signals acquired by IMD 402, such as can be received via a communication link 411. The external system 405 can include a local external IMD programmer. The external system 405 can include a remote patient management system that can monitor patient status or adjust one or more therapies, such as from a remote location.

The communication link 411 can include one or more of an inductive telemetry link, a radio-frequency telemetry link, or a telecommunication link, such as an internet connection. The communication link 411 can provide for data transmission between the IMD 402 and the external system 405. The transmitted data can include, for example, real-time physiologic data acquired by the IMD 402, physiologic data acquired by and stored in the IMD 402, therapy history data or data indicating IMD operational status stored in the IMD 402, one or more programming instructions to the IMD 402, such as to configure the IMD 402 to perform one or more actions that can include physiologic data acquisition, such as using programmably specifiable sensing electrodes and configuration, device self-diagnostic test, or delivery of one or more therapies.

Portions of the IMD 402 or the external system 405 can be implemented using hardware, software, or any combination of hardware and software. Portions of the IMD 402 or the external system 405 may be implemented using an application-specific circuit that can be constructed or configured to perform one or more particular functions or can be implemented using a general-purpose circuit that can be programmed or otherwise configured to perform one or more particular functions. Such a general-purpose circuit can include a microprocessor or a portion thereof, a microcontroller or a portion thereof, or a programmable logic circuit, or a portion thereof. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. While described with reference to the IMD 402, the CRM system 500 could include a subcutaneous medical device (e.g., subcutaneous ICD, subcutaneous diagnostic device), wearable medical devices (e.g., patch-based sensing device), or other external medical devices.

Figure 5:
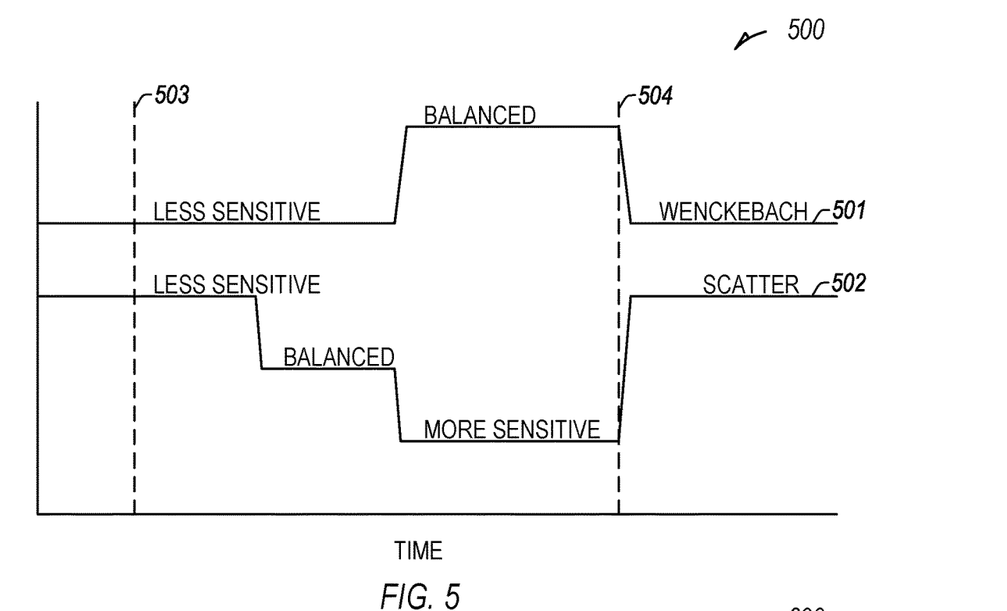
FIG. 5 illustrates example threshold adjustments for first and second detection thresholds.

FIG. 5 illustrates example threshold adjustments 500 for first and second arrhythmia detection thresholds 501, 502 progressing in time from a time of a first detected arrhythmia event 503 to a detected low-confidence arrhythmia event 504 (or a rejected event, or a determination or confirmation of no arrhythmia event, etc.). The first and second arrhythmia detection thresholds 501, 502 can be applied to one or more respective detection parameters, either separately or in combination, to detect an event, a potential event, or a long-duration event, etc. In other examples, one or more additional detection thresholds having different adjustments in time can be used; the adjustments are not limited to one or more of the first and second arrhythmia detection thresholds 501, 502.

In an example, the first arrythmia event can be detected when a detection parameter fall below the first arrhythmia detection threshold 501 or exceed the second arrhythmia detection threshold 502, etc. In other examples, a first detection parameter must fall below the first arrhythmia detection threshold 501 and a second detection parameter must exceed the second arrhythmia detection threshold 502 to detect the first event. In other examples, other detection parameters or thresholds can be used to detect the first arrhythmia event. When the first or second detection parameters exceed the first arrhythmia detection threshold 501, falls below the second arrhythmia detection threshold 502, or both, the low-confidence arrhythmia event (or a rejected event, or determination or confirmation of no arrhythmia event, etc.) can be detected.

In an example, the first arrhythmia detection threshold 501 can include a Wenckebach detection threshold, and the first arrhythmia detection parameter can include a Wenckebach detection parameter or one or more other measures of atrioventricular block (AV block) indicative of impaired conduction between the atria and ventricles of the heart. Example Wenckebach or AV block detection parameters can include, among others, a p-wave to r-wave interval (PR interval), a mismatch in atrial and ventricular activations (e.g., 2-to-1 A to V activations, 3-to-1 A to V activations, 3-to-2 A to V activations, etc.), or one or more other parameters, etc. Before the time of the first detected arrhythmia event 503, and for a period of time thereafter, a measured first arrhythmia detection parameter can be compared to the first arrhythmia detection threshold 501 at first level (LESS SENSITIVE), different than a second level (BALANCED) having a higher sensitivity than the first level. A time (e.g., a predetermined time, such as 10 minutes, 30 minutes, 1 hour, 2 hours, etc.) after the time of the first detected arrhythmia event 503, the first level can transition to the second level. In other examples, other more sensitive thresholds can be used, having one or more other time periods after the time of the first detected arrhythmia event 503.

The second arrhythmia detection threshold 502 can include a scatter detection threshold, such as a time, variance, one or more common ranges, or other measure of rate or interval changes, and the second arrhythmia detection parameter can include an indication of a time, variance, rate, interval, or a statistical measure (e.g., median, average, clusters, etc.) between successive atrial or ventricular events (e.g., r-waves, etc.). Before the time of the first detected arrhythmia event 503, and for a period of time thereafter, a measured second arrythmia detection parameter can be compared to the second arrhythmia detection threshold 502 at a first level (LESS SENSITIVE), different than second and third levels (BALANCED and MORE SENSITIVE) having higher sensitivities than the first level. A first time (e.g., a predetermined time, such as 5 minutes, 10 minutes, 30 minutes, 1 hour, etc.) after the time of the first detected arrhythmia event 503, the first level can transition to the second level, and a second time after the time of the first detected arrhythmia event 503, the second level can transition to the third level. In other examples, other more or less sensitive thresholds can be used, having one or more other time periods after the time of the first detected arrhythmia event 503.

In various examples, the first and second arrhythmia detection thresholds can include one or more other detection thresholds, such as those illustrated in the references incorporated herein, including rate changes, rate change characteristics, depolarization intervals, morphology criterion, atrial activity scores, clustered depolarizations, etc.

Figure 6:
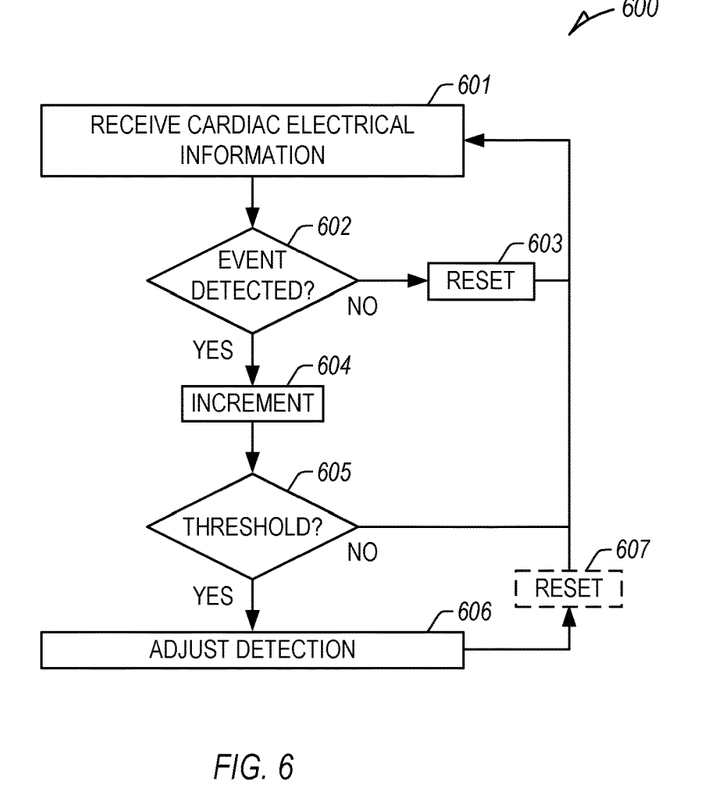
FIG. 6 illustrates an example method of adjusting first and second detection thresholds.

FIG. 6 illustrates an example method 600 of adjusting a set of arrhythmia parameters or at least one of a respective set of parameter thresholds, such as a long-duration arrhythmia event (e.g., a long-duration AF event, etc.), to increase sensitivity of an extended arrhythmia event indication detection using the adjusted set of arrhythmia parameters or at least one of the respective set of parameter thresholds.

At 601, cardiac electrical information is received, such as using a signal receiver circuit of a component of a medical system, such as a first ambulatory medical device, a medical device programmer, etc. The cardiac electrical information can be received from a cardiac sensor or one or more other devices (e.g., a second ambulatory medical device, etc.). In other examples, other physiologic information can be received by the signal receiver circuit, separate from or in combination with the cardiac electrical information, such as to detect an extended arrhythmia event indication (e.g., a long-duration AF event, etc.).

At 602, event detection can be performed, such as using an assessment circuit. In an example, a set of arrhythmia parameters for a detection window interval can be determined using the received cardiac electrical information of the subject, the other physiologic information, or combinations thereof. In an example, the set can include one arrhythmia parameter or multiple arrhythmia parameters. An initial arrhythmia event indication can be detected, for the detection window interval, using the determined set of arrhythmia parameters and a respective set of parameter thresholds, in certain examples, one parameter threshold for each of the set of arrhythmia parameters.

In an example, the set of arrhythmia parameters can be determined, and the initial arrhythmia event can be detected, for each of a plurality of detection window intervals, including, in certain examples, successive detection window intervals. If, at 602, an initial arrhythmia event indication is detected, indicative of an arrhythmia event (e.g., a potential arrhythmia event, a confirmed or classified arrhythmia event, etc.), a timer or a count can be incremented at 604.

If, at 605, the count or time does not exceed a threshold amount, such as a first time or a first count of detection window intervals, etc., the method returns to 601. If, at 605, the count or time exceeds the threshold amount, event detection can be adjusted at 606. In an example, the set of arrhythmia parameters can be adjusted to increase sensitivity of detection of extended arrhythmia event. In other examples, at least one of the respective set of parameter thresholds can be adjusted to increase sensitivity of detection of extended arrhythmia event. In an example, an extended arrhythmia event indication can be detected using the adjusted set of arrhythmia parameters and the adjusted at least one of the respective set of parameter thresholds. At 603, or optionally at 607, the count or time can be reset.

Figure 7:
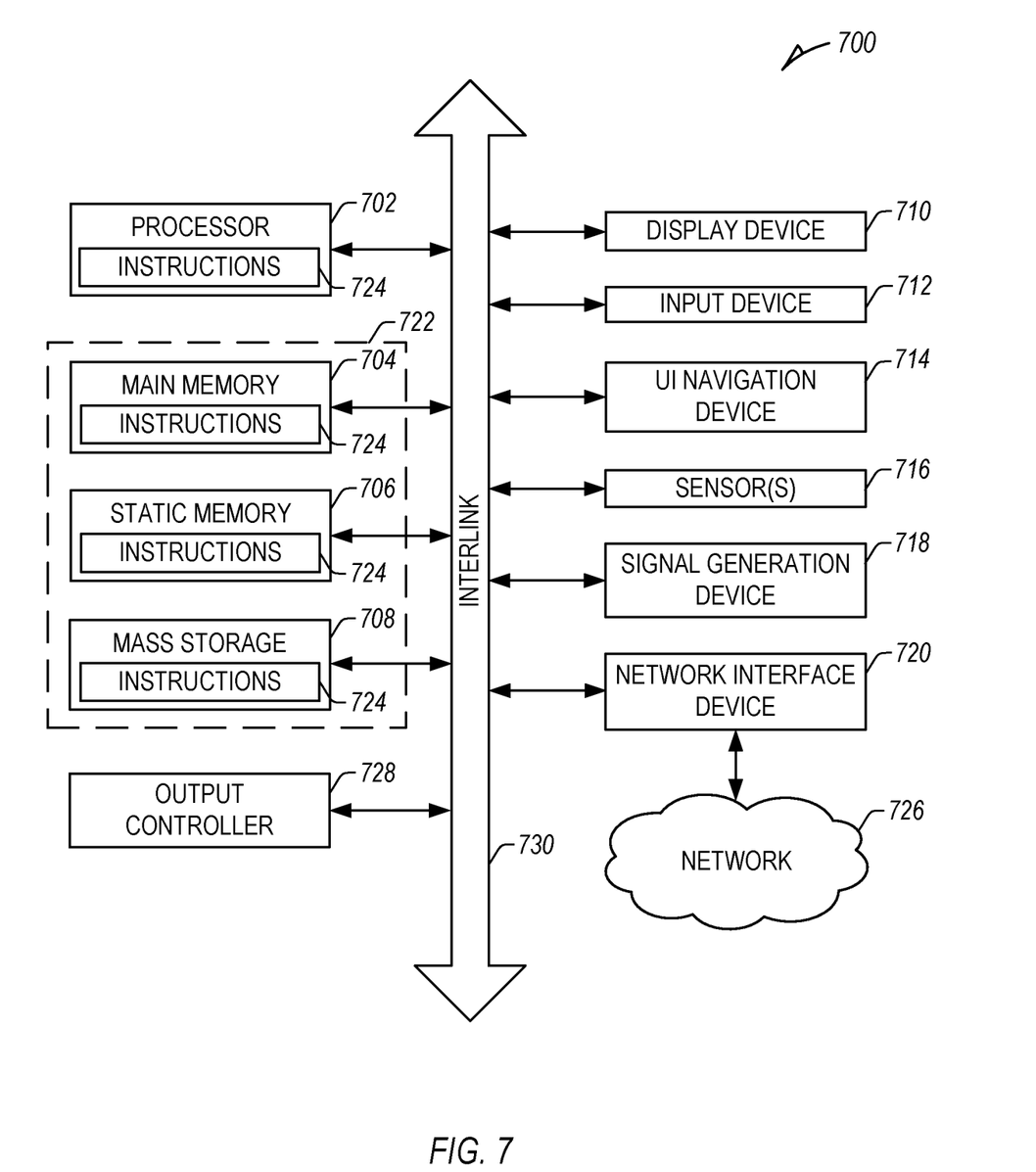
FIG. 7 illustrates a block diagram of an example machine upon which any one or more of the techniques discussed herein may perform.

FIG. 7 illustrates a block diagram of an example machine 700 upon which any one or more of the techniques (e.g., methodologies) discussed herein may perform. Portions of this description may apply to the computing framework of one or more of the medical devices described herein, such as the IMD, the external programmer, etc. Further, as described herein with respect to medical device components, systems, or machines, such may require regulatory-compliance not capable by generic computers, components, or machinery. Before the first detected arrhythmia event 503

Examples, as described herein, may include, or may operate by, logic or a number of components, or mechanisms in the machine 700. Circuitry (e.g., processing circuitry) is a collection of circuits implemented in tangible entities of the machine 700 that include hardware (e.g., simple circuits, gates, logic, etc.). Circuitry membership may be flexible over time. Circuitries include members that may, alone or in combination, perform specified operations when operating. In an example, hardware of the circuitry may be immutably designed to carry out a specific operation (e.g., hardwired). In an example, the hardware of the circuitry may include variably connected physical components (e.g., execution units, transistors, simple circuits, etc.) including a machine-readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuitry in hardware via the variable connections to carry out portions of the specific operation when in operation. Accordingly, in an example, the machine-readable medium elements are part of the circuitry or are communicatively coupled to the other components of the circuitry when the device is operating. In an example, any of the physical components may be used in more than one member of more than one circuitry. For example, under operation, execution units may be used in a first circuit of a first circuitry at one point in time and reused by a second circuit in the first circuitry, or by a third circuit in a second circuitry at a different time. Additional examples of these components with respect to the machine 700 follow.

In alternative embodiments, the machine 700 may operate as a standalone device or may be connected (e.g., networked) to other machines. In a networked deployment, the machine 700 may operate in the capacity of a server machine, a client machine, or both in server-client network environments. In an example, the machine 700 may act as a peer machine in peer-to-peer (P2P) (or other distributed) network environment. The machine 700 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

The machine (e.g., computer system) 700 may include a hardware processor 702 (e.g., a central processing unit (CPU), a graphics processing unit (GPU), a hardware processor core, or any combination thereof), a main memory 704, a static memory (e.g., memory or storage for firmware, microcode, a basic-input-output (BIOS), unified extensible firmware interface (UEFI), etc.) 706, and mass storage 708 (e.g., hard drive, tape drive, flash storage, or other block devices) some or all of which may communicate with each other via an interlink (e.g., bus) 730. The machine 700 may further include a display unit 710, an alphanumeric input device 712 (e.g., a keyboard), and a user interface (UI) navigation device 714 (e.g., a mouse). In an example, the display unit 710, input device 712, and UI navigation device 714 may be a touch screen display. The machine 700 may additionally include a signal generation device 718 (e.g., a speaker), a network interface device 720, and one or more sensors 716, such as a global positioning system (GPS) sensor, compass, accelerometer, or one or more other sensors. The machine 700 may include an output controller 728, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

Registers of the processor 702, the main memory 704, the static memory 706, or the mass storage 708 may be, or include, a machine-readable medium 722 on which is stored one or more sets of data structures or instructions 724 (e.g., software) embodying or utilized by any one or more of the techniques or functions described herein. The instructions 724 may also reside, completely or at least partially, within any of registers of the processor 702, the main memory 704, the static memory 706, or the mass storage 708 during execution thereof by the machine 700. In an example, one or any combination of the hardware processor 702, the main memory 704, the static memory 706, or the mass storage 708 may constitute the machine-readable medium 722. While the machine-readable medium 722 is illustrated as a single medium, the term "machine-readable medium" may include a single medium or multiple media (e.g., a centralized or distributed database, and/or associated caches and servers) configured to store the one or more instructions 724.

The term "machine-readable medium" may include any medium that is capable of storing, encoding, or carrying instructions for execution by the machine 700 and that cause the machine 700 to perform any one or more of the techniques of the present disclosure, or that is capable of storing, encoding, or carrying data structures used by or associated with such instructions. Non-limiting machine-readable medium examples may include solid-state memories, optical media, magnetic media, and signals (e.g., radio frequency signals, other photon-based signals, sound signals, etc.). In an example, a non-transitory machine-readable medium comprises a machine-readable medium with a plurality of particles having invariant (e.g., rest) mass, and thus are compositions of matter. Accordingly, non-transitory machine-readable media are machine-readable media that do not include transitory propagating signals. Specific examples of non-transitory machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 724 may be further transmitted or received over a communications network 726 using a transmission medium via the network interface device 720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 720 may include one or more physical jacks (e.g., Ethernet, coaxial, or phone jacks) or one or more antennas to connect to the communications network 726. In an example, the network interface device 720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding, or carrying instructions for execution by the machine 700, and includes digital or analog communications signals or other intangible medium to facilitate communication of such software. A transmission medium is a machine-readable medium.

Figure 8:
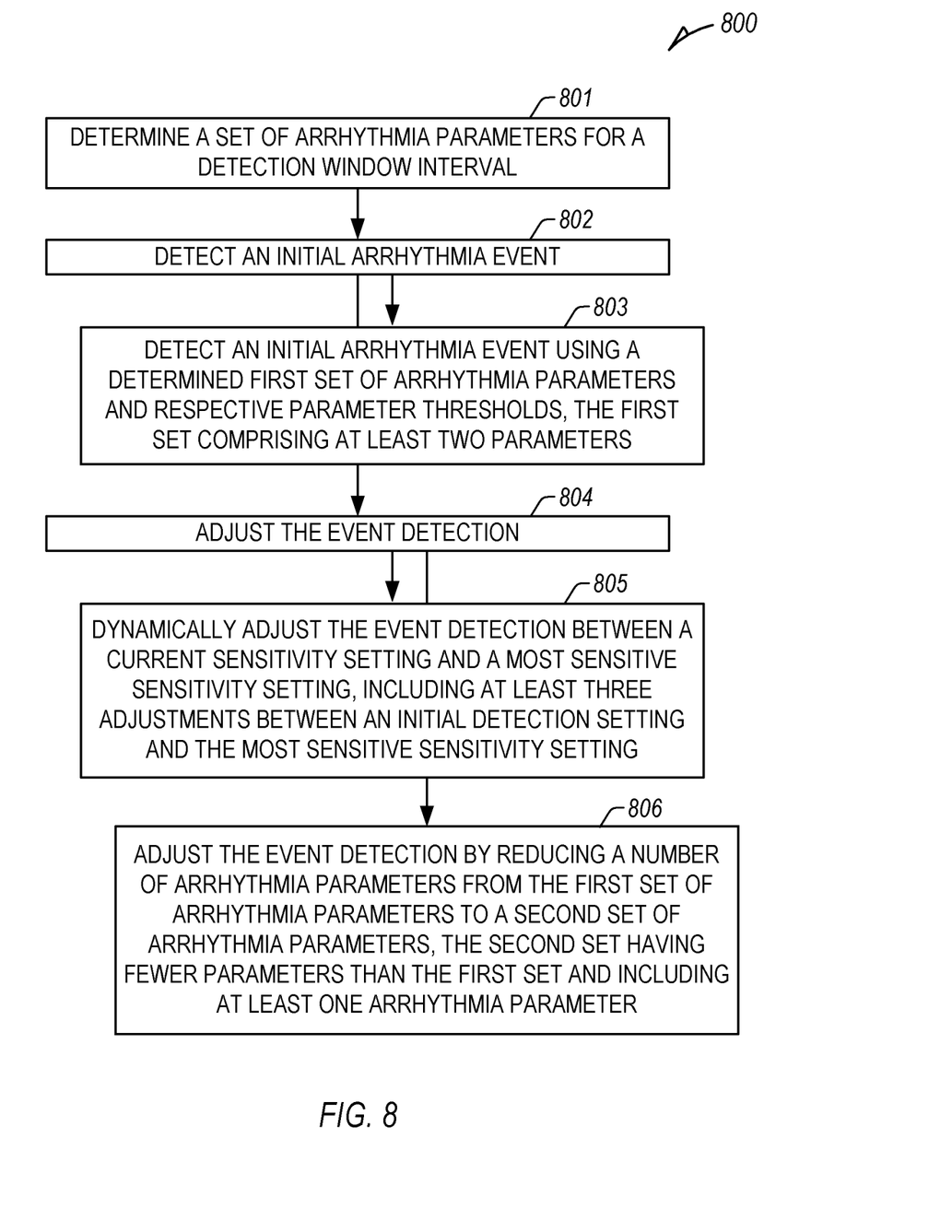
FIG. 8 illustrates an example method of adjusting an event detection.

FIG. 8 illustrates an example method 800 of adjusting an event detection. At 801, a set of arrhythmia parameters is determined for a detection window interval. At 802, an initial arrhythmia event is detected, including an optional step at 803. At 804, the event detection is adjusted, including one or more optional steps at 805 or 806.

Various embodiments are illustrated in the figures above. One or more features from one or more of these embodiments may be combined to form other embodiments. Method examples described herein can be machine or computer-implemented at least in part. Some examples may include a computer-readable medium or machine-readable medium encoded with instructions operable to configure an electronic device or system to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:
1. A system, comprising:
a signal receiver circuit configured to receive cardiac electrical information of a subject; and
an assessment circuit for performing event detection, the assessment circuit configured to:
determine a set of arrhythmia parameters for a detection window interval using the received cardiac electrical information of the subject, the set including at least one arrhythmia parameter; and
detect, for the detection window interval, an initial arrhythmia event indication using the determined set of arrhythmia parameters and a respective set of parameter thresholds,
wherein, after a threshold amount of detection window intervals detecting the initial arrhythmia event indication, the assessment circuit is configured to dynamically adjust the event detection for subsequent detection window intervals until an exit criteria is detected, comprising to:

dynamically adjust, between a current sensitivity setting and a most sensitive sensitivity setting, including at least three adjustments between an initial detection setting and the most sensitive sensitivity setting, at least one of the respective set of parameter thresholds to increase sensitivity of an extended arrhythmia event indication detection using the at least one of the respective set of parameter thresholds.

2. The system of claim 1, wherein the threshold amount of detection window intervals detecting the initial arrhythmia event indication comprises a threshold amount of successive detection window intervals detecting the initial arrhythmia event indication.

3. The system of claim 2, wherein, to dynamically adjust the event detection for subsequent detection window intervals until an exit criteria is detected, the assessment circuit is configured to dynamically adjust the set of arrhythmia parameters and the at least one of the respective set of parameter thresholds to increase the sensitivity of the extended arrhythmia event indication detection.

4. The system of claim 3, wherein the assessment circuit is configured to detect, for a subsequent detection window interval, subsequent to the successive detection window intervals, an extended arrhythmia event indication using the adjusted set of arrhythmia parameters and the adjusted at least one of the respective set of parameter thresholds.

5. The system of claim 3, wherein, to determine the set of arrhythmia parameters, the assessment circuit is configured to determine a first set of arrhythmia parameters, the first set comprising at least two arrhythmia parameters,
wherein, to detect the initial arrhythmia event indication, the assessment circuit is configured to detect the initial arrhythmia event indication using the determined first set of arrhythmia parameters and respective parameter thresholds,
wherein, to adjust the event detection, the assessment circuit is configured to reduce a number of arrhythmia parameters from the first set of arrhythmia parameters to a second set of arrhythmia parameters having fewer arrhythmia parameters than the first set, and to:
determine a second set of arrhythmia parameters for a subsequent detection window interval, subsequent to the successive detection window intervals using the received cardiac electrical information of the subject, the second set smaller than the first set and including at least one arrhythmia parameter; and
detect, for the subsequent detection window interval, an extended arrhythmia event indication using the determined second set of arrhythmia parameters using the determined second set of arrhythmia parameters and respective parameter thresholds.

6. The system of claim 2, wherein, to adjust the event detection, the assessment circuit is configured to:
adjust at least one of the respective set of parameter thresholds; and
detect, for a subsequent detection window interval, subsequent to the successive detection window intervals, an extended arrhythmia event indication using the determined set of arrhythmia parameters and the adjusted at least one of the respective set of parameter thresholds.

7. The system of claim 1, wherein the threshold amount of detection window intervals detecting the initial arrhythmia event indication comprises the threshold amount in a first number of detection windows.

8. The system of claim 1, wherein the event detection includes atrial fibrillation (AF) detection,
wherein the adjusted event detection includes a long-duration AF event detection, and
wherein the threshold amount is at least one of a time threshold or a counter threshold.

9. The system of claim 1, wherein the assessment circuit is configured to output the detected extended arrhythmia event indication to a user or to process to effect a treatment.

10. A system, comprising:
a signal receiver circuit configured to receive cardiac electrical information of a subject; and
an assessment circuit for performing event detection, the assessment circuit configured to:
determine a first set of arrhythmia parameters for a detection window interval using the received cardiac electrical information of the subject; and
detect, for the detection window interval, an initial arrhythmia event indication using the determined first set of arrhythmia parameters and respective parameter thresholds, the first set of arrhythmia parameters comprising at least two parameters;
wherein, after a threshold amount of successive detection window intervals detecting the initial arrhythmia event indication, the assessment circuit is configured to adjust the event detection by reducing a number of arrhythmia parameters from the first set of arrhythmia parameters to a second set of arrhythmia parameters, comprising:
determine the second set of arrhythmia parameters for a subsequent detection window interval, subsequent to the successive detection window intervals, using the received cardiac electrical information of the subject, the second set having fewer parameters than the first set and including at least one arrhythmia parameter; and
detect, for the subsequent detection window interval, an extended arrhythmia event indication using the determined second set of arrhythmia parameters using the determined second set of arrhythmia parameters and respective parameter thresholds.

11. The system of claim 10, wherein, after a threshold amount of successive detection window intervals detecting the initial arrhythmia event indication, the assessment circuit is configured to adjust the event detection, comprising:
adjust at least one of the respective set of parameter thresholds; and
detect, for a subsequent detection window interval, subsequent to the successive detection window intervals, an extended arrhythmia event indication using the determined set of arrhythmia parameters and the adjusted at least one of the respective set of parameter thresholds.

12. A system, comprising:
a signal receiver circuit configured to receive cardiac electrical information of a subject; and
an assessment circuit for performing event detection, the assessment circuit configured to:
determine a set of arrhythmia parameters for a detection window interval using the received cardiac electrical information of the subject, the set including at least one arrhythmia parameter; and
detect, for the detection window interval, an initial arrhythmia event indication using the determined set of arrhythmia parameters and a respective set of parameter thresholds, wherein, after a threshold amount of detection window intervals detecting the initial arrhythmia event indication, the assessment circuit is configured to dynamically adjust the event detection for subsequent detection window intervals until an exit criteria is detected, comprising to:

dynamically adjust, between a current sensitivity setting and a most sensitive sensitivity setting, including at least three adjustments between an initial detection setting and the most sensitive sensitivity setting, the set of arrhythmia parameters to increase sensitivity of an extended arrhythmia event indication detection using the adjusted set of arrhythmia parameters.

13. The system of claim 12, wherein the threshold amount of detection window intervals detecting the initial arrhythmia event indication comprises a threshold amount of successive detection window intervals detecting the initial arrhythmia event indication.

14. The system of claim 13, wherein, to dynamically adjust the event detection for subsequent detection window intervals until an exit criteria is detected, the assessment circuit is configured to dynamically adjust the set of arrhythmia parameters and at least one of the respective set of parameter thresholds to increase the sensitivity of the extended arrhythmia event indication detection.

15. The system of claim 14, wherein the assessment circuit is configured to detect, for a subsequent detection window interval, subsequent to the successive detection window intervals, an extended arrhythmia event indication using the adjusted set of arrhythmia parameters and the adjusted at least one of the respective set of parameter thresholds.

16. The system of claim 13, wherein, to determine the set of arrhythmia parameters, the assessment circuit is configured to determine a first set of arrhythmia parameters, the first set comprising at least two arrhythmia parameters, wherein, to detect the initial arrhythmia event indication, the assessment circuit is configured to detect the initial arrhythmia event indication using the determined first set of arrhythmia parameters and respective parameter thresholds, wherein, to adjust the event detection, the assessment circuit is configured to reduce a number of arrhythmia parameters from the first set of arrhythmia parameters to a second set of arrhythmia parameters having fewer arrhythmia parameters than the first set, and to:

determine a second set of arrhythmia parameters for a subsequent detection window interval, subsequent to the successive detection window intervals using the received cardiac electrical information of the subject, the second set smaller than the first set and including at least one arrhythmia parameter; and detect, for the subsequent detection window interval, an extended arrhythmia event indication using the determined second set of arrhythmia parameters using the determined second set of arrhythmia parameters and respective parameter thresholds.

17. The system of claim 13, wherein, to adjust the event detection, the assessment circuit is configured to:

adjust at least one of the respective set of parameter thresholds; and detect, for a subsequent detection window interval, subsequent to the successive detection window intervals, an extended arrhythmia event indication using the determined set of arrhythmia parameters and the adjusted at least one of the respective set of parameter thresholds.

18. The system of claim 12, wherein the threshold amount of detection window intervals detecting the initial arrhythmia event indication comprises the threshold amount in a first number of detection windows.

19. The system of claim 12, wherein the event detection includes atrial fibrillation (AF) detection, wherein the adjusted event detection includes a long-duration AF event detection, and wherein the threshold amount is at least one of a time threshold or a counter threshold.

20. The system of claim 12, wherein the assessment circuit is configured to output the detected extended arrhythmia event indication to a user or to process to effect a treatment.

* * * * *